US005627052A

United States Patent [19]
Schrader

[11] Patent Number: 5,627,052
[45] Date of Patent: May 6, 1997

[54] METHODS FOR THE PRODUCTION OF PROTEINS WITH A DESIRED FUNCTION

[75] Inventor: John W. Schrader, Vancouver, Canada

[73] Assignee: B.R. Centre, Ltd., Vancouver, Canada

[21] Appl. No.: 464,261

[22] Filed: Jun. 5, 1995

Related U.S. Application Data

[63] Continuation of Ser. No. 88,601, Jul. 6, 1993, abandoned, which is a continuation of Ser. No. 561,984, Aug. 2, 1990, abandoned.

[51] Int. Cl.$^6$ ................................................. A61K 39/395
[52] U.S. Cl. ................. 435/69.6; 435/172.3; 530/387.1; 530/388.24
[58] Field of Search ........................... 530/387.1, 388.24; 435/70.21, 172.3, 69.6

[56] References Cited

U.S. PATENT DOCUMENTS

| | | | |
|---|---|---|---|
| 4,035,316 | 7/1977 | Yen et al. | 260/2.5 B |
| 4,138,383 | 2/1979 | Rembaum et al. | 260/29.7 H |
| 4,143,203 | 3/1979 | Rigopulos et al. | 428/407 |
| 4,157,323 | 6/1979 | Yen et al. | 260/29.7 M |
| 4,230,685 | 10/1980 | Senyei et al. | 424/12 |
| 4,357,142 | 11/1982 | Schall, Jr. et al. | 23/230 B |
| 4,363,634 | 12/1982 | Schall, Jr. | 23/230 B |
| 4,452,773 | 6/1984 | Molday | 424/1.1 |
| 4,550,075 | 10/1985 | Bacquet et al. | 435/7 |
| 4,618,577 | 10/1986 | Handley et al. | 435/7 |
| 4,689,310 | 8/1987 | Kramer et al. | 436/512 |

FOREIGN PATENT DOCUMENTS

| | | |
|---|---|---|
| 265384A2 | 4/1988 | European Pat. Off. |
| 2485739 | 12/1981 | France. |
| 63-33338A | 2/1988 | Japan. |
| 2-171199 | 7/1990 | Japan. |

OTHER PUBLICATIONS

Zhang et al. Hum. Antibiod. Hybridomas 1990 1(1) 42–46.
Huse et al., "Generation of a Large Combinatorial Library of the Immunoglobulin Repertoire in Phage Lambda," *Science* 246:1275–1281, 1989.
Lazar et al., "Transforming Growth Factor α: Mutation of Aspartic Acid 47 and Leucine 48 Results in Different Biological Activities," *Molecular and Cellular Biology* 8(3): 1247–1252, 1988.
Burgess et al., "Possible Dissociation of the Heparin–Binding and Mitogenic Activities of Heparin–Binding (Acidic Fibroblast) Growth Factor–1 from Its Receptor–Binding Activities by Site–Directed Mutagenesis of a Single Lysine Residue," *Journal of Cell Biology* 111: 2129–2138, 1990.
Goding, J., in *Monoclonal Antibodies: Principles and Practice*, 2nd Ed., 1986, pp. 76–89.
Sahagan et al., "A Genetically Engineered Murine/Human Chimeric Antibody Retains Specificity for Human Tumor–Associated Antigen," *Journal of Immunology* 137(3): 1066–1074, 1986.
Orlandi et al., "Cloning Immunoglobulin Variable Domains for Expression by the Polymerase Chain Reaction," *Proc. Natl. Acad. Sci. USA* 86: 3833–3837, 1989.
Liu et al., "Chimeric Mouse–Human IgG1 Antibody That Can Mediate Lysis of Cancer Cells," *Proc. Natl. Acad. Sci. USA* 84: 3439–3443, 1987.
Kanagawa, O., "Antibody–Mediated Activation of T Cell Clones as a Method for Screening Hybridomas Producing Antibodies to the T Cell Receptor," *Journal of Immunological Methods* 110: 169–178, 1988.
Allen, P., "Construction of Murine T–T–Cell Hybridomas," in *Monoclonal Antibody Production Techniques and Applications*, L.B. Schook ed., Marcel Dekker, Inc. New York, 1987, pp. 25–35.
Aggarwal and Bringman, "Production and Purification of Lymphokines and Their Monoclonal Antibodies" in *Monoclonal Antibody Production Techniques and Applications*, L.B. Schook ed., Marcel Dekker, Inc. New York, 1987, pp. 173–187.
Kingsman and Kingsman, "Biotechnology," in *Genetic Engineering: An Introduction to Gene Analysis and Exploitation in Eukaryotes*, Blackwell Scientific Publications, Oxford, 1988, pp. 414–456.
Larrick et al., "Polymerase Chain Reaction Using Mixed Primers: Cloning of Human Monoclonal Antibody Variable Region Genes from Single Hybridoma Cells," *Bio/Technology* 7: 934–938, 1989.
Huston et al., "Protein Engineering of Antibody Binding Sites: Recovery of Specific Activity in an Anti–Digoxin Single–Chain Fv Analogue Produced in *Escherichia coli*," *Proc Natl. Acad. Sci. USA* 85: 5879–5883, 1988.
Riechmann et al., "Reshaping Human Antibodies for Therapy," *Nature* 332: 323–327, 1988.
Frohman et al., "Rapid Production of Full–Length cDNAs from Rare Transcripts: Amplification Using a Single Gene–Specific Oligonucleotide Primer," *Proc. Natl. Acad. Sci. USA* 85: 8998–9002, 1988.
Loh et al., "Polymerase Chain Reaction with Single–Sided Specificity: Analysis of T Cell Receptor σ Chain," *Science* 243: 217–220, 1989.

(List continued on next page.)

*Primary Examiner*—Lila Feisee
*Assistant Examiner*—Julie E. Reeves
*Attorney, Agent, or Firm*—Seed and Berry LLP

[57] ABSTRACT

The present invention provides a method for producing proteins with a desired function, generally comprising the steps of (a) providing a population of antibody-forming cells suspected of containing at least one cell capable of producing an antibody exhibiting a desired function; (b) suspending the population of antibody-forming cells in a medium, the medium having an indicator system incorporated therein, the indicator system also being capable of indicating the presence and location of a cell which forms antibodies exhibiting the desired function; (c) identifying a cell forming an antibody exhibiting the desired function; (d) isolating the identified antibody-forming cell from the medium; (e) determining the amino acid sequence of the variable region or a portion thereof which coffers the desired function of the antibody produced by the isolated antibody-forming cell; and (f) synthesizing a protein with a desired function, the protein containing the amino acid sequence of the variable region or portion thereof which confers the desired function.

38 Claims, No Drawings

OTHER PUBLICATIONS

Samoilovich et al., "Hybridoma Technology: New Developments of Practical Interest," *Journal of Immunological Methods* 101: 153–170, 1987.

Price, P., "Hybridoma Technology," *Advances in Cell Culture* 4: 157–177, 1985.

Bayer and Wilchek, "The Avidin–Biotin Complex as a Tool in Molecular Biology," *TIBS* 3(11) N257–N259, 1978.

Wilchek and Bayer, "The Avidin–Biotin Complex in Bioanalytical Applications," *Analytical Biochemistry* 171:1–32, 1988.

Bayer and Wilchek, "The Use of the Avidin–Biotin Complex as a Tool in Molecular Biology," *Methods of Biochemical Analysis*:1–45, 1980.

METHODS FOR THE PRODUCTION OF PROTEINS WITH A DESIRED FUNCTION

CROSS REFERENCE TO RELATED APPLICATIONS

This application is a continuation of application Ser. No. 08/088,601, filed Jul. 6, 1993, now abandoned, which is a continuation of application Ser. No. 07/561,984, filed Aug. 2, 1990, now abandoned.

DESCRIPTION

1. Technical Field

The present invention relates generally to the production of proteins with a desired function, and more specifically, to methods for identifying specific antibodies or other proteins which can bind to a specific substance, and activate, catalyze, or otherwise effect a desired function. These methods also provide for modification of the identified protein, and for production of the protein in large quantities.

2. Background of the Invention

Proteins have long been recognized for their crucial role in many biological activities. Proteins in general have many capabilities, including, among others, the ability to activate or catalyze reactions, as well as the ability to cleave or modify other proteins, carbohydrates and organic compounds.

Although recombinant DNA techniques have been developed for producing useful proteins, one of the most difficult aspects of these processes lies in first detecting and isolating proteins of a desired biological activity. Once the protein has been detected and isolated in sufficient quantities, the structure of the gene encoding the protein may be deduced and used to produce the protein by recombinant DNA techniques. Various methods have been developed for detecting proteins of a desired biological activity, including a wide variety of biological assays. For example, proteins may be detected through the use of enzyme assays, binding assays which measure the affinity of proteins for specific substrates, or assays which detect the stimulation of cell growth.

One particular class of proteins, antibodies, has been identified and developed for therapeutic and diagnostic uses. Antibodies have a vast diversity of structure and function which allows virtually any given substance to be recognized. For example, antibodies may be found which are able to specifically bind to and/or neutralize particular toxins, viruses, parasites, and other etiologic agents. Additionally, antibody molecules have been identified that can mimic the functions of other proteins, such as growth factors, hormones, or enzymes. While methods have been developed to produce potentially unlimited quantities of specific monoclonal antibodies, these methods are severely limited in their application due to the difficulty of isolating hybridomas from antibody-forming cells that occur only at low frequencies. More specifically, antibody-forming cells which produce antibodies with a restricted specificity, or with a particular functional activity such as the ability to mimic the function of an enzyme or hormone represent antibody-forming cells which are very difficult to isolate which are very difficult to isolate because they form only a small proportion of the antibodies that bind enzymes or hormone receptors. Moreover, some desired antibodies may be formed only by certain species of animals for which the hybridoma technology is unavailable.

Somatic cell hybridization is the most widely used method for producing monoclonal antibodies (see Kohler and Milstein, *Nature* 256:495, 1975). Although various modifications have been adopted in an effort to improve upon this method, such as in vitro immunization, electrofusion, and receptormediated strategies (see *Monoclonal Antibody Production Techniques and Applications*, Lawrence B. Schook (ed.), Marcel Dekker Inc., 1987), the method of somatic cell hybridization has remained essentially unchanged. Briefly, within this method, an animal is immunized with an antigen of interest inducing the development of an immune response by the animal to the antigen of interest. The animal is then sacrificed and organs with large deposits of B cells (such as the spleen and lymph nodes) are removed and fused to an immortal cell line, such as NS-1. The resulting hybridomas are then screened for specificity to the antigen of interest and subcloned until a single specific clone is obtained (see Paul G. Price, "Hybridoma Technology," *Advances in Cell Culture*, Vol. 4, 1985).

There are, however, many deficiencies with this method. One deficiency is that monoclonal antibodies cannot readily be made from human cells. The basic method requires immunization of an animal followed by the removal of its spleen and lymph nodes, which, of course, is not feasible for humans. Even if other techniques are used, such as in vitro immunization using human cells, there are other difficulties to overcome.

For example, it has proven difficult to find suitable human myeloma-fusion partners; human-human hybrids are not as stable and do not produce as great a quantity of antibody as can be attained in mouse-mouse fusion systems. Another difficulty is that human cells contain various repressed lethal viruses which may be activated and expressed upon hybridization and subsequent recombination. These viruses can be infectious, and pose issues of health and safety for lab workers. Furthermore, it is difficult to absolutely purify away all lethal viruses from the monoclonal antibodies, and thus such antibodies could not readily be used therapeutically for humans.

Another difficulty of the basic method is obtaining rare antibodies. The size of the original pool of hybridomas is limited by the number of stable antibody clones that can be generated and screened in a reasonable time and by the intrinsic inefficiency of the process. Thus, of the antibody cells present in the population of immunized cells that are subjected to the fusion process, only a small fraction form stable antibody-producing hybrids and are available to screen for the desired antibody. Furthermore, antibodies must be subcloned in a tedious growth and subcloning process during which the desired antibody-forming cell may be lost. If the desired antibody is formed by only a small fraction of antibodyforming cells involved in an immune response, for example, an antibody which mimics an enzyme, the likelihood that this antibody will be produced by any of the stable hybrids available for screening is correspondingly small.

Yet another difficulty of the basic method is in varying the species of origin of the monoclonal antibody. While monoclonal antibodies can be produced from rodents, such as mice, rats and hamsters, they cannot readily be produced from other species, such as humans, as discussed above. Since the antibody repertoire differs for different animals, it would be advantageous if these intrinsic differences in repertoire could be exploited in order to produce a monoclonal antibody of a desired function or specificity.

Thus, there remains a need in the art for a method of producing proteins that replicate the binding characteristics and desired function of particular antibodies. The present

SUMMARY OF THE INVENTION

Briefly stated, the present invention provides a method for producing proteins with a desired function. In one aspect, the method comprises the steps of (a) providing a population of antibody-forming cells suspected of containing at least one cell capable of producing an antibody with a desired function; (b) suspending the population of antibody-forming cells in a medium, the medium having an indicator system incorporated therein, the indicator system also being capable of indicating the presence and location of a cell which forms antibodies exhibiting a desired function; (c) identifying a cell forming an antibody exhibiting the desired function; (d) isolating the identified antibody-forming cell from the medium; (e) determining the amino acid sequence of the variable region or a portion thereof which confers the desired function of the antibody produced by the isolated antibody-forming cell; and (f) synthesizing a protein with a desired function, the protein containing the amino acid sequence of the variable region or portion thereof conferring the desired function. Within an alternative embodiment, step (f) above is replaced with the following steps: (f) incorporating the DNA sequence corresponding to the amino acid sequence of the variable region or portion thereof conferring the desired function into a vector, the vector being capable of directing the expression and secretion of the protein with a desired function; (g) transfecting the vector into a host cell; (h) growing the vector into a host cell; and (i) isolating the protein with the desired function.

Within further embodiments, subsequent to the steps of isolating the antibody-forming cell, the method further comprises the steps of (a) recovering RNA from the isolated antibody-forming cell; (b) generating cDNA from the RNA; and (c) amplifying the cDNA of the variable region or a portion thereof which confers the desired function of the antibody produced by the isolated antibody-forming cell. As an alternative to steps (b) and (c), the following steps may be performed: (b) amplifying the RNA of the variable region or a portion thereof which confers the desired function of the antibody produced by the isolated antibody-forming cell; and (c) generating cDNA from the RNA Within yet another alternative, steps (a), (b) and (c) are replaced with the following steps: (a) recovering DNA from the isolated antibody-forming cell; and (b) amplifying the DNA of the variable region or a portion thereof which confers the desired function of the antibody produced by the isolated antibody-forming cell.

Within yet another embodiment, subsequent to the step of determining the amino acid sequence, the amino acid sequence of the portion conferring the desired function is optimized such that the desired function is enhanced.

Within another aspect of the present invention, a method is provided for producing a protein with a desired function, comprising: (a) providing a population of antibody-forming cells suspected of containing at least one cell capable of producing an antibody exhibiting a desired function; (b) suspending the population of antibody-forming cells in a medium, the medium having an indicator system incorporated therein, the indicator system being capable of indicating the presence and location of a cell which forms antibodies exhibiting the desired function; (c) identifying a cell forming an antibody exhibiting the desired function; (d) isolating the identified antibody-forming cell from the medium; (e) recovering RNA from the isolated antibody-forming cell; (f) generating cDNA from the RNA; (g) amplifying the cDNA of the portion of the variable region or a portion thereof which confers the desired function of the antibody produced by the isolated antibody-forming cell; (h) incorporating the amplified cDNA into a vector capable of directing the expression and secretion of a protein with the desired function; (i)transfecting the vector into a host cell; (j) growing the host cell in an appropriate medium; and (k) isolating the protein with the desired function from the host cell. Within a further embodiment of this invention, steps (f), (g) and (h) are replaced with the following steps: (f) amplifying the RNA of the variable region or a portion thereof which confers the desired function of the antibody produced by the isolated antibody-forming cell; (g) generating cDNA from the RNA; and (h) incorporating the cDNA into a vector capable of directing the expression and secretion of a protein with the desired function.

In one embodiment of the present invention, the indicator system comprises a layer of cells whose growth viability or function is affected by antibodies exhibiting a desired function produced by the isolated antibody-forming cells. These antibodies have an effect analogous to a protein selected from the group consisting of IL-1α, IL-1β, IL-2, IL-3, IL-4, IL-5, IL-6, IL-7, IFN-α, IFN-γG-CSF, M-CSF, GM-CSF, TNF-α, TGF-β, erythropoietin, EGF, PDGF, and the ligand of the kit protein. In another embodiment, the indicator system comprises one or more pathogenic microorganisms, and a layer of cells susceptible to infection by the microorganisms, wherein the antibodies exhibiting a desired function are identified as those which affect the pathogenicity of the microorganism. In another embodiment, the layer of cells susceptible to infection by the microorganisms is adhered to a glass slide or petri dish. In yet another embodiment, the indicator system comprises a set of two cell types selected from the group consisting of cells of distinct HLA histocompatibility antigen types, blood group antigen types, or tumor cells and normal cells of the same lineage. In yet another embodiment, the indicator system comprises erythrocytes or other particles coated with antigen, and the antibodies of a desired function are identified as those which bind to the coated antigen, causing the particles to agglutinate.

In another embodiment of the present invention, the indicator system comprises erythrocytes coated with antigen such that the antibodies of a desired function are identified as those which bind to the coated antigen and lyse cells in the presence of complement. Anti-immunoglobulin antibodies may be added such that complement fixation is enhanced. In another embodiment, the indicator system comprises a substrate, and the antibody exhibiting a desired function is identified as that which modifies the substrate in a detectable manner. In yet another embodiment of the invention, the indicator system comprises a complexing factor, and the antibody-forming cell is identified as that which binds to the complexing factor, forming a rosette. Suitable complexing factors include erythrocytes bound to an antigen, particles bound to an antigen, and microorganisms.

Also provided by the present invention are proteins which are produced by the above described methods.

These and other aspects of the present invention will become evident upon reference to the following detailed description.

DETAILED DESCRIPTION OF THE INVENTION

Prior to setting forth the invention, it may be helpful to an understanding thereof to define certain terms to be used hereinafter.

Indicator System: An indicator system manifests a specific desired activity in response to antibody on the surface of or released into the vicinity of an antibody-forming cell, thus permitting identification and isolation of the cell-producing antibody with the desired function.

Antibody-Forming Cell: A cell which forms antibodies, such as a B-lymphocyte or its progeny including the plasma cell. These cells may either secrete antibodies (antibody-secreting cells) or maintain antibodies on the surface of the cell without secretion into the cellular environment. Other antibodyforming cells within the scope of the present invention include bacterial cells, mammalian cells, yeast or other cells which form antibodies as a result of the artificial expression of introduced immunoglobulin genes or parts thereof according to the general methods described by Winter and colleagues (see E. S. Ward et al., *Nature* 341:544, 1989; see also R. Orlandi et al., *Proc. Natl. Sci. USA* 866:3833, 1989) and by Lerner and colleagues (see W. D. Huse et al., "Generation of a Large Combinatorial Library of the Immunoglobulin Repertoire in Phage Lambda," *Science* 246:1275, 1989).

Medium: A substance that provides the minimum requirements for the short-term maintenance of cellular integrity and cellular structures. These requirements may be met by, for example, an isotonic buffer.

Nutrient Medium: A substance that contains carbon and nitrogen sources as well as other supplements which are required for the viability of cultured cells. Such media may be obtained from commercial sources or formulated from published recipes. (See catalogs of the American Type Culture Collection, Rockville, Md.)

As noted above, the present invention simplifies the mass production of proteins having a desired function. These proteins have the same binding characteristics as the antibody produced by a single carefully selected, antibody-forming cell and possess a biological activity which allows them to bind, catalyze, activate, or otherwise effect a desired function. The present invention 1.5 allows the rapid identification and exploitation of such antibody-forming cells, even if present at only a very low frequency.

An antibody-forming cell may be identified among antibody-forming cells obtained from an animal which has either been immunized with a selected substance, or which has developed an immune response to an antigen as a result of disease. Animals may be immunized with a selected antigen using any of the techniques well known in the art suitable for generating an immune response (see Handbook of Experimental Immunology D. M. Weir (ed.), Vol 4, Blackwell Scientific Publishers, Oxford, England, 1986). Within the context of the present invention, the phrase "selected antigen" includes any substance to which an antibody may be made, including, among others, proteins, carbohydrates, inorganic or organic molecules, and transition state analogs that resemble intermediates in an enzymatic process. Suitable antigens include, among others, biologically active proteins, hormones, cytokines, and their cell surface receptors, bacterial or parasitic cell membrane or purified components thereof, and vital antigens. Representative cytokines include IL-1$\alpha$, IL-1$\beta$, IL-2, IL-3, IL-4, IL-5, IL-6, IL-7, IFN-$\alpha$, IFN-$\gamma$, G-CSF, M-CSF, GM-CSF, TNF-$\alpha$, TGF-$\beta$, erythropoietin, EGF, PDGF, and the ligand of the kit protein. Representative viral antigens include reverse transcriptase core and envelope proteins, for example, gp 120, the envelope protein of HIV-1. As will be appreciated by one of ordinary skill in the art, antigens which are of low immunogenicity may be accompanied with an adjuvant or hapten in order to increase the immune response (for example, complete or incomplete Freund's adjuvant) or with a carrier such as keyhole limpet hemocyanin (KLH).

Many warm-blooded animals, such as humans, rabbits, mice, rats, sheep, cows or pigs may be immunized in order to obtain antibody-forming cells. However, mice and rats are generally preferred because of their ease in handling, well-defined genetic traits, and the fact that they may be readily sacrificed. Procedures for immunizing animals are well known in the art. Briefly, animals are injected with the selected antigen against which it is desired to raise antibodies. The selected antigen may be accompanied by an adjuvant or hapten, as discussed above, in order to further increase the immune response. Usually the substance is injected into the peritoneal cavity, beneath the skin, or into the muscles or bloodstream. The injection is repeated at varying intervals and the immune response is usually monitored by detecting antibodies in the serum using an appropriate assay that detects the properties of the desired antibody. Large numbers of antibody-forming cells can be found in the spleen and lymph node of the immunized animal. Thus, once an immune response has been generated, the animal is sacrificed, the spleen and lymph nodes are removed, and a single cell suspension is prepared using techniques well known in the art.

Antibody-forming cells may also be obtained from a subject which has generated the cells during the course of a selected disease. For instance, antibody-forming cells from a human with a disease of unknown cause, such as rheumatoid arthritis, may be obtained and used in an effort to identify antibodies which have an effect on the disease process or which may lead to identification of an etiological agent or body component that is involved in the cause of the disease. Similarly, antibody-forming cells may be obtained from subjects with disease due to known etiological agents such as malaria or AIDS. These antibodyforming cells may be derived from the blood or lymph nodes, as well as from other diseased or normal tissues. Antibody-forming cells may be prepared from blood collected with an anticoagulant such as heparin or EDTA. The antibody-forming cells may be further separated from erythrocytes and polymorphs using standard procedures such as centrifugation with Ficoll-Hypaque (Pharmacia, Uppsula, Sweden). Antibody-forming cells may also be prepared from solid tissues such as lymph nodes or tumors by dissociation with enzymes such as collagenase and trypsin in the presence of EDTA.

Antibody-forming cells may also be obtained by culture techniques such as in vitro immunization. Examples of such methods are described by C. R. Reading in *Methods in Enzymology* 21:18–33 (J. J. Langone, H. H. van Vunakis (eds.), Academic Press Inc., N.Y.). Briefly, a source of antibody-forming cells, such as a suspension of spleen or lymph node cells, or peripheral blood mononuclear cells are cultured in medium such as RPMI 1640 with 10% fetal bovine serum and a source of the substance against which it is desired to develop antibodies. This medium may be additionally supplemented with amounts of substances known to enhance antibody-forming cell activation and proliferation such as lipopolysaccharide or its derivatives or other bacterial adjuvants or cytokines such as IL-1, IL-2, IL-4, IL-5, IL-6, GM-CSF, and IFN-$\gamma$. To enhance immunogenicity, the selected antigen may be coupled to the surface of cells, for example, spleen cells, by conventional techniques such as the use of biotin/avidin as described below.

Antibody-forming cells may also be obtained from very early monoclonal or oligoclonal fusion cultures produced by conventional hybridoma technology. The present invention is advantageous in that it allows rapid selection of antibody-forming cells from unstable, interspecies hybridomas, e.g., formed by fusing antibody-forming cells from animals such as rabbits, humans, cows, pigs, cats, and dogs with a murine myeloma such NS-1.

Antibody-forming cells may be enriched by methods based upon the size or density of the antibody-forming cells relative to other cells. An example of the use of Percoll to separate cells according to density is described by van Mourik and W. P. Zeizlmaker in *Methods in Enzymology* 121:174–182 (J. J. Langone, H. H. van Vunakis (eds.), Academic Press Inc., N.Y.). Gradients of varying density of solutions of bovine serum albumin can also be used to separate cells according to density. (See N. Moav and T. N. Harris, *J. Immunol* 105:1512, 1970; see also Raid, D. J. in SELECTED METHODS IN CELLULAR IMMUNOLOGY, B. Mishell and S. Shiigi (eds.), W. H. Freeman and Co., San Francisco, 1987). The fraction that is most enriched for desired antibody-forming cells can be determined in a preliminary procedure using the appropriate indicator system (as described below) in order to establish the antibody-forming cells.

In order to identify single antibody-forming cells producing antibodies of a desired function, the cells suspected of possessing the desired function are suspended in a medium having an "indicator system" incorporated therein. Within the context of the present invention, "having an indicator system incorporated therein" includes not only indicator systems which are located within the medium containing the antibody-forming cells, but indicator systems which are positioned contiguous to the medium, such that the affects of the antibodies produced by the antibody-forming cells may be manifested in the indicator system. Additionally, the effects of the antibodies may be transferred to the indicator system by other means. For example, a membrane may be positioned contiguous to the medium in order to adsorb antibodies which diffuse from the antibody-forming cells. Suitable membranes include nitrocellulose or other materials which bind proteins. To further enhance local adsorption of the antibodies, the membrane may be coated with proteins such as an antibody or antibodies which is specific for immunoglobulins of the same species as that of the antibody-forming cell. The membrane acts as a replica upon which the distribution of antibodyforming cells in the media may be reproduced. When the membrane is placed into one of the indicator systems described below, antibody-forming cells producing antibodies of a desired function may be detected on the membrane. An antibody-forming cell which forms a positive in the indicator system may be located by aligning the membrane with the gelified media. If the antibody-forming cells are bacterial cells, the colonies or plaques may similarly be replicated by plaque or colony lifts using methods known to those skilled in the art.

It will be evident to those skilled in the art that in addition to establishing the presence of cell-producing antibodies of a desired function within a population of cells, the indicator system may also be utilized to optimize procedures for immunization regimens, to determine sources of antibody-forming cells which produce antibodies which confer the desired function, or to determine the efficacy of protocols for enriching antibody-forming cells.

The medium incorporating the indicator system should at a minimum provide the requirements for the short-term maintenance of cellular integrity and structures. The medium may be in the form of a liquid layer, or a gelified layer. Methods for gelifying media are well known in the art.

Particularly preferred gelified media contain about 0.3%–0.6% agar or about 1.0% methyl cellulose. Adherence of gelified media to glass may be facilitated by precoating the glass. For example, glass slides may be brushed with a hot solution of 0.1% (w/v) agarose and allowed to dry, followed by addition of a gelified medium. If a viable cell is required after isolation of the antibody-forming cell, then it is preferred to use a nutrient medium with appropriate supplements in order to aid cell viability. Particularly preferred media is RPMI 1640 (Gibco, Grand Island, N.Y.), with 10% Fetal Bovine Serum (Hyclone Serum) and 20 mM HEPES (Gibco). Within certain embodiments of the present invention, the indicator cells, and in some cases the antibody-forming cells, may be adhered to the surface of a microscope slide or dish culture. Adherence may be induced by coating the surface of the slide or culture dish with poly-L-lysine (Sigma Chemical Company, Mo.) or fibronectin (Sigma Chemical Co.). Within one embodiment, 1 mg/ml of poly-L-lysin, or 100/µg/ml of fibronectin is used to coat a slide or culture dish surface for about one hour, followed by timing with Phosphate Buffered Saline (PBS).

The components of the indicator system are selected so as to manifest activity on the surface of an antibody-forming cell. Additionally, in cases where antibody is secreted from the surface of the antibody-forming cell, antibody will diffuse into the nearby vicinity of the cell. Thus, in indicator systems which produce plaques (as discussed below), diffusion of antibody into the surrounding indicator system results in a plaque with an individual antibody-forming cell located centrally therein. Antibody-forming cells should be diluted within the indicator system to a density which allows selection of an individual or small number of antibody-forming cells. If it is unclear which cell is responsible for the activity indicated by the indicator system, or in order to confirm the activity, the selected cell(s) may be retested for their ability to produce antibodies with the desired effect by transfer to a fresh indicator system.

Through use of the methods described herein, the desired function of the antibody identified by the indicator system may be replicated in another antibody or other protein, allowing production of the antibody or protein with the desired function in virtually unlimited quantities. By this means a variety of useful proteins with desired functions may be produced, including proteins with the function of mimicking the activity of biologically active factors, such as IL-1α, IL1β, IL-2, IL-3, IL-4, IL-5, IL-6, IL-7, IFN-γ, G-CSF, M-CSF, GM-CSF, TNF-α, TGFβ, erythropoietin, EGF, PDGF, the ligand of the kit protein, or of other biologically active substances. The present invention also allows the production of proteins with a function analogous to antibodies produced only in human beings, such as antibodies that neutralize a microorganism that is pathogenic only in humans (e.g., the HIV-1 virus). Such proteins may be used in the passive immunotherapy of viral diseases, such as AIDS, or in identifying important vaccine candidates among antigens of a microorganism including, among others, viruses, parasites, yeast, and bacteria. The proteins could also be used to discriminate between human histocompatibility antigens, blood group antigens, or to bind to autoantigens and aid in their characterization. The proteins can also be used as catalysts to carry out enzymatic reactions such as the cleavage of proteins.

In one aspect of the present invention, the indicator system comprises a layer of cells whose growth, viability, or function is affected by antibodies produced by the isolated antibody-forming cell. For example, to identify an antibody-forming cell which produces an antibody that neutralizes a growth factor or other biologically active molecule, the indicator system contains indicator cells which respond to the presence of the biologically active molecule. The biologically active molecule may cause cells to survive rather than die, to change morphology, or to spread and adhere to a surface. Interference with the action of the biologically active factor in the vicinity of the antibody-forming cell indicates the presence of an antibody which neutralizes the growth factor or biologically active molecule.

In contrast, the indicator system may be prepared with a layer of cells, excluding a necessary biologically active molecule. With the exclusion of the biologically active molecule, antibodies that are able to mimic the particular action of the biologically active molecule and reproduce the desired change in the indicator cell, e.g., by influencing viability, morphology, adherence, or other properties, may be detected. Antibodies so detected may exhibit biological activity analogous to a protein such as IL-1α, IL-1 β, IL-2, IL-3, IL-4, IL-5, IL-6, IL7, IFN-α, IFN-γ, G-CSF, M-CSF, GM-CSF, TNFα, TGF-β, erythropoietin, EGF, PDGF or the ligand of the kit protein.

Within another aspect of the present invention, antibodies may be identified which neutralize the pathogenicity of a microorganism. Within the context of the present invention, microorganisms include viruses, parasites, bacteria, and yeasts or fungi. To identify antibodies neutralizing the pathogenicity of a microorganism, susceptible cells and the microorganism are mixed in the indicator system with a source of antibody-forming cells. Desired antibodies are identified by the lack of a cytopathic effect on susceptible cells in the region of the antibody-forming cell. If the indicator cells are adherent, they may be allowed to adhere to glass slides or petri dish before the gelified medium containing antibody-forming cells is added. As noted above, if the indicator cells are nonadherent, poly-L-lysine or fibronectin may be used to coat the surfaces and thus aid the adherence of these cells. Within a preferred embodiment, a suspension of the indicator cells in medium is applied to the surface at a concentration of approximately $2 \times 10^6$ cells/cm$^2$ and allowed to stand for thirty minutes to an hour at 37° C. After the cells have adhered the surplus medium may be removed.

Examples of such indicator systems include baby rabbit kidney (BRK) cells and vaccinia virus, or human T-lymphocyte cell lines and HIV-1, any of which may be obtained from conventional sources such as the American Type Culture Collection (Rockville, Md.). Antibody-forming cells which release an antibody that neutralizes infection by the virus are identified by their central position in a plaque of indicator cells that have been protected from infection and have not undergone a cytopathic effect.

Within one embodiment of the present invention, a Balb/C mouse is immunized with an inactivated preparation of vaccinia virus. After several immunizations, the mouse is sacrificed and the spleen and lymph nodes are removed. The spleen and lymph nodes are disassociated to form a single-cell suspension of antibody-forming cells, and are mixed together with baby rabbit kidney cells and allowed to adhere to poly-L-lysine treated glass or plastic. After incubating at 3720 C. in nutrient medium to allow recovery of metabolic activity of the antibody-forming cells, the nutrient medium is removed and replaced with a thin layer of nutrient medium containing 0.5% methyl cellulose together with a titre of vaccinia virus shown in pilot experiments to be just sufficient to produce confluent lysis of the baby rabbit kidney cells over a 24-hour period. The indicator system is incubated in a highly humidified $CO_2$ incubator for 24 hours. Antibodyforming cells that produce antibody which neutralizes the virus result in plaques of live baby rabbit kidney cells (which may be identified with phase contrast microscopy) surrounding a centrally positioned antibody-forming cell.

Within another aspect of the present invention, the indicator system comprises a mixture of two or more cell types. Examples include cells of distinct HLA histocompatibility antigen types, different blood group antigen types, and tumor cells and normal cells of the same lineage. The two types of cells should be distinguishable by morphology, or by marking of one of the populations by for example, a fluorescent marker. Antibodies produced by the antibody-forming cell are then selected based upon their ability to agglutinate or lyse one cell of the pair.

Within one embodiment, the indicator system is utilized to detect a cell producing an antibody that discriminates between a tumor cell and a normal cell of the same cell lineage or tissue type as the tumor cell. This may be accomplished by the desired antibody agglutinating or including complement mediated lysis of the tumor cells, but not the normal cells in the vicinity of the antibody-secreting cell. If the tumor cell and the normal cell cannot be readily distinguished by morphology, they may be distinguished by labeling one of the pair with a dye, for example, with a fluorescent dye, such as fluorescein isothiocyanate. Cells may be readily coupled with this dye by incubation with 100/µg/ml of fluorescein isothiocyanate (Molecular Probes, Plano, Tex.) in phosphate-buffered saline at pH 8 for thirty minutes. The cells are then washed with phosphate-buffered saline and 10% fetal bovine serum. Cells may also be stained with a colored substance such as trinitro-phenol (TNP) using 2-4-6 trinitro-phenol benzene sulphonic acid by exposing them to a solution of 10 mg/ml in 0.28 cacodylate buffer, pH 6.9 for 30 minutes at room temperature (SELECTED METHODS IN CELLULAR IMMUNOLOGY, B. Mishell and S. Shiigi (eds.), W. H. Freeman and Co., San Francisco, 1987, pp. 112–113).

Within a preferred embodiment, antibody forming cells at concentrations ranging from $10^3$ to $10^5$ cells/ml are mixed together with tumor and nontumor cells at a concentration of $10^6$ cells/mi. The mixture is supplemented with a source of complement, such as guinea pig serum that has been absorbed with sheep erythrocytes, at a dilution such as 1 in 16 by final volume, together with an enhancing anti-immunoglobulin serum. The enhancing anti-immunoglobulin serum is generally prepared utilizing either a rabbit or goat which has been immunized and has developed antibodies against the immunoglobulins of the animal species from which antibody-forming cells were derived. This serum is diluted as determined by pretrial experiments, generally in the range of 1 in 80 to 1 in 400 by final volume. Antibody-forming cells which generate an antibody that binds only to tumor cells, will result in a plaque of tumor cells, leaving only nontumor cells surrounding a centrally located antibody-forming cell. Phase contrast microscopy with or without the addition of a dye such as trypan blue may be used to identify plaques or regions where cells have been lysed by the action of antibodies, the enhancing anti-immunoglobulin antibodies, and complement.

Within another aspect of the present invention, the indicator system comprises erythrocytes or other particles coated with antigen, and the antibody exhibiting a desired function is identified as that which binds to the antigen, thereby causing the particles to agglutinate or lyse in the region surrounding the antibody-forming cell. Many particles may be used in the context of the present invention, including, among others, sheep erythrocytes and artificial particles, such as beads (Polysciences, Warrington, Pa.) or magnetic beads (Robbin Scientific, Mountain View, Calif.). A number of methods for coating particles with antigens are known to those skilled in the art. These include the use of chromic chloride (see C. R. Parish and J. A. Hayward, *Proc, Roy. Soc.* 187:47, 1974) or water-soluble carbodiimide (see E. S. Golub et al., *J. Immunol* 100:133, 1968).

In a preferred embodiment, a biotin/avidin coupling system is utilized for plaque or "rosetting" assays in order to detect antibodies that bind to a particular antigen. Briefly, cells (for example, sheep red blood cells) are washed thoroughly by centrifugation with phosphate-buffered saline (PBS). Half a ml of packed red blood cells is then suspended in 5 ml of PBS which has been adjusted to pH 8–8.3 by the addition of sodium hydroxide. A succinimide ester derivative of biotin dissolved in dimethyl sulfoxide is added to the PBS, and the mixture is agitated at room temperature for about one hour. The red cells are then washed with PBS, pH 7, and may be stored in the refrigerator for up to two weeks.

The selected antigen which is to be coupled to the red cells is dialyzed overnight in 0.1M $NaHCO_3$ at a concentration of 1 mg/ml. The succinimide ester of biotin is dissolved in dimethyl sulfoxide (DMSO) and added to the solution of the protein, and the mixture is held at room temperature for one hour. The biotin-conjugated protein is then dialyzed overnight against PBS with 0.1% sodium azide and stored by refrigeration.

To conjugate biotin-coupled proteins to the red blood cells, 0.2 ml of packed biotin-conjugated red cells are first incubated at room temperature with an excess of avidin (2 ml of 1 mg/ml avidin in PBS, pH 7). The red cells are separated from the avidin solution by centrifugation and are washed with PBS, pH 7. The avidin-coated red cells are then added to a solution of the biotin-coupled protein and the mixture held at room temperature for one hour. The red cells are then separated from the solution by centrifugation and washed three times in PBS, pH 7.

The optimal conditions for coating the red cells with individual proteins may be determined empirically in the chosen indicator system by varying the concentration of biotinylated protein or the degree of biotinylation of the protein. Coating of red cells with biotin may be monitored using fluorescein-conjugated avidin and fluorescence microscopy or flow cytometry. Likewise, successful coating of the red cells with the protein may be assessed with a fluorescein-conjugated antibody directed against that protein.

The antigen-coated red cells are preferably used in an assay based upon the ability of specific antibodies, through complement-mediated lysis, to produce a plaque of hemolysed red cells around an antibody-forming cell secreting the desired antibody. If agar is used to gelify the medium, anticomplementary activity should be neutralized by inclusion of 1 mg/ml DEAE dextran, Mr $5 \times 10^5$ to $2 \times 10^6$ (Pharmacia Fine Chemicals). To enhance complement-mediated hemolysis of antigen-coated erythrocytes by the desired antibodies, anti-immunoglobulin antibodies or "enhancing" antisera may be included in the indicator system. This antisera or antibody is specific for immunoglobulins of all classes or of a desired class of immunoglobulin in the species from which the antibody-forming cells are derived, and is able to fix complement when bound to antibody molecules bound to the antigen-coated erythrocytes. Within one embodiment, enhancing antisera derived from a sheep immunized with murine immunoglobulins is utilized to enhance hemolysis of murine antibodies. The optimal concentration of enhancing antisera may be determined by observing the concentration enabling detection of the greatest number of hemolytic plaques in a plaque assay. Within this embodiment the indicator system contains a source of antibody-forming cells (e.g., nucleated spleen cells from a mouse immunized with an antigen, against which it is desired to produce an antibody), antigen-coated sheep erythrocytes (e.g., at $5 \times 10^8$/ml), a source of complement, (e.g., guinea pig serum preabsorbed with two equal volumes of sheep erythrocytes at a final concentration of 10% by volume), and enhancing serum prepared as described above at a final concentration of 0.5%, all in nutrient medium buffered with 20 mM HEPES. The mixture is introduced dropwise under a layer of warm (37° C.) paraffin oil on a transparent surface, e.g., a glass slide, and incubated for one hour.

Antibody-forming cells which produce an antibody which binds to the antigen coated on the sheep erythrocytes may be identified by their central position in plaques of hemolysed red blood cells with an inverted phase-contrast microscope. To exclude the possibility that the antibody-forming cell is producing an antibody that is not specific for the antigen which is coupled to the erythrocyte, but rather the biotinylated indicator, erythrocytes, or avidin, the following test is performed. Each candidate antibody-forming cell is picked up using a fine glass pipette and micromanipulator and is transferred to a second indicator system, again containing complement and enhancing serum, but in which antigen-coated sheep erythrocytes have been substituted with biotinylated sheep erythrocytes coated only with avidin. This indicator system is prepared as described above; if a plaque forms, the candidate cell is discarded as the antibody produced cannot be specific for the desired protein. If a plaque does not form in 40 minutes the cell is transferred to a warmed droplet containing the original indicator system, i.e., antigen-coated erythrocytes, complement and enhancing serum. Plaque formation in 40 minutes is taken as confirmatory evidence that the candidate cell is indeed producing an antibody specific for the desired antigen.

Within an alternative embodiment, the indicator system contains equal numbers of antigen-coated erythrocytes and erythrocytes lacking the antigen (biotinylated erythrocytes coated only with avidin). Plaques formed by cells forming antibodies to the desired antigen will be "cloudy," as the non-antigen coupled erythrocytes will not be lysed. In contrast, any "background" plaques caused by cells fortuitously producing antibodies against non-antigen coupled erythrocytes will be clear as both coupled and uncoupled erythrocytes will be lysed.

Within another aspect of the present invention the indicator system may be used to identify antibody-forming cells, such as B lymphocytes, which produce antibodies of a desired specificity, but which express antibody on their surface rather than by secreting it.

For example, a "rosetting" procedure may be utilized to identify antibody-forming cells which produce antibodies that bind to a complexing factor, thus forming a rosette. The complexing factor may be sheep erythrocytes or other particles, such as polystyrene beads which have been coupled to an antigen. The erythrocytes or other particles may be coupled by any of the methods well known in the art, including the biotin/avidin coupling system discussed above. Alternatively, the complexing factor may be a microorganism such as a virus, parasite, yeast, or bacteria. To detect antibody-forming cells that bind to the desired particles, a population containing candidate antibodyforming cells, e.g., nucleated spleen cells from an immunized mouse, is mixed in medium with the particles. The mixture can be centrifuged at 200 g for 10 minutes and resuspended by gentle pipetting. Antibody-forming cells producing the desired antibody may be identified by the attached particles using inverted microscopy and picked up using a fine pipette and micromanipulators. Generally, it is preferable to first enrich the population of cells to which the particles have bound. For example, the complexes or rosettes which form due to the antigen-antibody interactions may also be enriched by various physical methods, including methods which are dependent on density, magnetic, fluorescent, or other properties of the rosettes. More specifically, rosettes formed by antibody-forming cells and coated erythrocytes may be enriched using a Ficoll-Hypaque gradient. (See C. R. Parish and J. A. Hayward, *Proc. Roy. Soc.* 13:117, 1974.) If the antigen is coupled to magnetic particles, cells binding the antigen-coated particles may be enriched by placing a magnet under part of a plastic flask or disk containing the cell suspension and decanting cells that are not attracted to the magnet by bound particles. The individual antibody-forming cells in the rosettes may be identified under a microscope and isolated by micromanipulation.

Nonspecific antibody-forming cells may also be separated using the above techniques prior to the formation of rosettes with antigen-coated erythrocytes. Briefly, within one embodiment, a cell population containing B lymphocytes is mixed in medium with a suspension of control non-antigen-coated erythrocytes, e.g., coated with biotin and exposed to avidin and washed (without treatment with the biotin-coated antigen) at a final concentration of 5% by volume. The mixture is gently agitated at room temperature for 60 minutes. Rosettes consisting of B lymphocytes with adherent erythrocytes are separated from the remainder of the nucleated cells, for example by centrifugation using Ficoll-Hypaque (Pharmacia, Uppsula, Sweden). This procedure depletes the population of B lymphocytes reactive with erythrocytes, biotin, or avidin. The procedure may then be repeated with erythrocytes coated with the antigen to enrich B lymphocytes reactive with that antigen. Individual antibody-forming cells that have bound the complexing factor (antigen-coated) erythrocytes may then be identified and isolated using an inverted microscope.

Other indicator systems may be employed to detect antibodies with a desired catalytic function. Within this aspect of the present invention, the indicator system comprises a substrate, and the antibody exhibiting a desired function is identified as that which modifies the substrate in a detectable manner. Within one embodiment, antibody-forming cells are obtained from animals immunized with chemical analogues of transition-states which occur during catalysis by enzymes. These chemical analogues are designed to mimic in their shape and charge distribution intermediate structures formed in the course of an enzymatic reaction (see R. A. Lerner and S. J. Benkovic, *Bioessays* 4:107–12, 1988). Lerner and colleagues (see B. L. Iverson and R. A. Lerner, *Science* 243:1184–8, 1989) have also described another approach wherein antibodies are raised against a complex including a substrate (a peptide) and cofactor (metal complex) in order to produce antibodies which catalyze specific hydrolysis of the glycine-phenylalanine peptide bond along with a metal complex cofactor.

Within another embodiment, antibody-forming cells that produce antibodies that activate or inactivate a protein such as an enzyme may be identified by including that protein in the indicator system. In one embodiment, a population of antibody-forming cells from an animal, e.g., a mouse immunized with an analogue or analogues of a transition-state occurring during catalysis of a peptide bond, is mixed with an indicator system containing mouse erythrocytes and the precursor of the toxin, aerolysin, of *Aeromonas hydrophila* (J. T. Beckley et al., *Can. J. Biochem*, 59(6):430–5, 1981). Proteolytic cleavage of this precursor at a number of peptide bonds susceptible to a variety of known proteases activates the toxin (S. P. Howard and J. T. Buckley, *J. Bacteriol.* 163(1):336–40, 1985). Because the active toxin will lyse erythrocytes, antibody-forming cells secreting an antibody with proteolytic activity will be surrounded by a hemolytic plaque.

Within yet another embodiment, an antibody capable of activating plasminogen is identified using an indicator system in which antibody-forming cells, a gelling agent such as agar and nutrient medium are added to a mixture of plasma and a source of casein such as skim milk powder. In this indicator system, a cell that produces an antibody that activates plasminogen by cleaving it and generating plasmin is located by its central position in a plaque where the opacity of the skim milk is cleared by the local proteolysis of the casein by plasmin.

Within other embodiments, the indicator system may contain a chromogenic, fluorogenic, colored, or fluorescent substrate designed such that the function of the desired antibody, e.g., cleavage of the substrate, may be identified by the local generation or loss of color or fluorescence. For example, the action of the desired antibody could result in the local generation of a fluorescent or colored product or the local loss of a fluorescent or colored substance in the vicinity of the cell producing the antibody responsible for the cleavage. Within one embodiment, peptide substrates coupled with amido-4-methyl coumarin release a fluorescent compound when cleaved resulting in a ring of fluorescence surrounding the antibody-forming cell. Specific peptides can be used for different enzymes, e.g., N-acetyl-ala-pro-ala-7-amido-4-methyl coumarin is a specific fluorogenic substate for elastase (see Zimmerman et al., *Anal. Biochem*, 78:47, 1977).

Antibodies which are labeled with fluorescent markers such as fluorescein or a phycobilliprotein may also be used as a tool to identify the products of the action of catalytic antibodies in the vicinity of an antibody-forming cell. Furthermore, a developing monoclonal antibody that recognizes and forms complexes with the products of the breakdown of fibrin (see M. J. Elms et al., *Thromb. Res.* 30:521, 1983) will form a precipitate around that antibody-forming cell and may thus be used to identify an antibody-forming cell secreting an antibody that cleaves fibrin.

Within yet another embodiment, a layer of gelatin may be utilized to detect an antibody with collagenase activity. Within this embodiment, gelatin may be visualized by coupling it with a colored or fluorescent substance, e.g., by derivatizing it with dinitrophenol using dinitrophenolisothiocyantate (Eastman Kodak Limited, Rochester, N.Y.), to yield a yellow product, or with fluorescein using fluorescein isothiocyanate (Molecular Probes, Plano, Tex.) to yield a fluorescent product. This derivatized gelatin is overlayed with a thin layer of agar containing antibody-forming cells. After incubation at 37° C. for one to four hours, the layer is washed with cold nutrient medium. A desired proteolytic antibody secreted by the antibody-forming cell will digest the gelatin into small fragments that may be washed away. Thus, areas lacking the colored or fluorescent gelatin are evidence of an antibody-forming cell which produces an antibody exhibiting the desired function.

In another embodiment, to detect an antibody capable of cleaving a peptide, that peptide is synthesized with an additional cysteine residue at the C-terminus and a biotin group at the N-terminus. The peptide is coupled by disulphide bonding to a convenient matrix with free thiol groups such as Thiol Sephoarose beads, (Pharmacia, Uppsula, Sweden). Indicator groups such as fluorescein-labeled avidin may be used to bind to the biotin and thus label the peptide on the beads. The labelled-peptide beads are then incorporated with a cell population containing antibody-forming cells in a layer of nutrient medium gelled with 0.5% agar in a petri dish or on a glass slide. The slide is incubated at 37° C. to allow an antibody with a proteolytic function to cleave the peptide, and thus to release the N-terminal fragment and its associated label. The agar is washed five times with 10 mls of cold 4° C. nutrient medium, and visualized with fluorescent microscopy. Plaques or areas that fail to fluoresce because of the cleavage of the fluorescein labeled peptides in the vicinity of an antibody-forming cell are located, and the central antibody-forming cell producing the desired antibody is identified.

As discussed above, the antibody-forming cell producing the desired antibody is generally located by its appearance and central position in the indicator plaque. An inverted phase-contrast microscope is a convenient instrument for this purpose. The antibody-forming cell may then be removed and placed in nutrient medium or grown in culture. In most cases, the antibody-forming cell can easily be removed with a fine glass pipette and a micromanipulator, although with practice, a skilled technician may not require the micromanipulator. If more than one cell is present in the indicator plaque, the cells may be placed in a fresh indicator system and incubated for a further period in order to determine which cell produced the desired response.

Once an antibody-forming cell has been identified and isolated, the desired functional properties of an antibody may then be transferred from one antibody to another antibody or protein. This may be accomplished by transferring the variable region, or a portion thereof which confers the desired function of the antibody produced by the isolated antibody-forming cell. Briefly, the special property of antibodies that allows the production by animals of a large variety of different antibody molecules, each with unique binding properties, is conferred by the presence in the antibody protein of two regions. One region, termed the "constant region," has the same structure in all antibodies from a particular isotype of the same species. The second region, termed the "variable region" (V-region), varies in its amino acid sequence from antibody to antibody, and it is this variability in structure that confers upon each particular antibody the special functional properties characteristic of that antibody. Antibody molecules are composed of two chains of amino acids (or polypeptides), each with a variable and constant region linked together by a disulphide bond. The larger chain is termed the "heavy chain" and the smaller the "light chain." The region of an antibody molecule that performs the desired function in the indicator systems described above (the "binding site") is made up of parts of both heavy and light chains. Thus, as discussed below, the sequences encoding the variable regions of the antibody produced by the antibody-forming cell may be transferred into another antibody or protein, thus conferring upon that antibody or protein the same function as that of the antibody produced by the isolated antibody-forming cell.

The variable regions of the light chain and the heavy chain each have three subregions where the variation in amino acid sequence between different variable regions is concentrated; these are termed "hypervariable regions." The amino acids that comprise these six hypervariable regions make up the binding site. The shape, charge, and other characteristics of the binding site determine the binding characteristics of the antibody and are termed the "complementarity determining regions" or CDRs. The key information that specifies the binding properties of an antibody is thus the amino acid sequence of the six CDRs, although in some cases the three CDRs of the heavy chain may confer a measurable and useful amount of specific binding for a particular protein. The amino acid sequence of the six CDRs is determined by the nucleotide sequence of corresponding parts of the gene encoding the variable regions of the heavy or light chains. Thus, the portion of the antibody produced by the antibody-forming cell that confers the desired function may be described largely by either the amino acid sequence of the respective six CDRs or by the nucleotide sequence of the DNA that encodes and specifies these CDRs.

As will be evident to one of ordinary skill in the art, the regions of cDNA which encode the CDR may be identified by alignment of the predicated amino acid sequence of the V region in question with other V regions from the same species or V regions from other species. Methods of sequence comparison have been described by Kabat et al. (see "Sequences of Proteins of Immunological Interest," U.S. Department of Health and Human Services, 1987). Thus, although the binding characteristics of a given antibody may be transferred to another protein by incorporating into that protein the entire variable regions of the heavy and light immunoglobulin chains, substitution of only a portion of the variable region, such as the six CDRs, may successfully transfer or graft binding characteristics of antibody produced by the antibody-forming cell to another antibody or protein (see L. Reichmann et al., Nature 332:325–27, 1988). Furthermore, the successful transfer of the desired function to another protein or antibody may be confirmed by expressing that protein in a cell and testing that cell in the indicator system used to isolate the antibody forming cell.

The variable regions or a portion thereof, such as the complementarity determining regions from the isolated antibody may be incorporated into a protein such as an antibody utilizing at least two alternative methodologies:

(I) The amino acid sequence of the variable regions or portions of the variable regions such as the CDR from the antibody produced by the isolated antibody-forming cell may be determined, and used to construct another antibody or other protein with a function similar to that of the isolated antibody. Once this amino acid sequence information has been acquired, it may be used to synthetically construct proteins with a desired function, or the DNA sequence encoding the desired amino acid sequence may be incorporated in the form of synthetic oligonucleotides into a vector capable of expressing a protein with the desired function from a host cell. It will be understood by those skilled in the art that the nucleic acid sequence can be used to predict the amino acid sequence, and vice versa.

(II) Within a second methodology, RNA from the isolated antibody-forming cell is used to generate cDNA, and cDNA encoding the desired functional region of the antibody is amplified and directly incorporated into an expression vector. Alternatively, the RNA may be amplified, used to construct cDNA, and the cDNA then incorporated into an expression vector. Within either of these alternatives, it is not necessary to determine the nucleic or amino acid sequence of the CDR, although in either case the RNA or DNA can be sequenced to determine the nucleotide sequences of the variable regions and, in particular, that of the respective CDRs. This information can be used to generate oligonucleotides that may be incorporated into a suitable vector. Alternatively, the information may be used to deduce amino acid sequences of the variable region and, in particular, the CDR and this information may be utilized to synthesize an antibody-like protein with the desired functional characteristics by chemical means.

I. AMINO ACID SEQUENCE DETERMINATION OF THE REGION CONFERRING THE DESIRED FUNCTIONAL PROPERTIES OF THE ANTIBODY PRODUCED BY THE ANTIBODY-FORMING CELL

Generally, within this method, the amino acid sequences of the variable regions or, more particularly, of the CDRs of the antibody produced by the isolated antibody-forming cell are determined, and incorporated into a selected protein. In general the binding properties of the antibody can be most confidently reproduced by reproducing the amino acid sequence of the entire heavy and variable regions of the light chains of the antibody molecule. However, in many cases, a useful protein with the binding properties of the antibody can be recreated by substitution of the amino acids of the CDRs of those variable regions for the CDRs of convenient heavy- and light-antibody chains. Reichman et al., in "Reshaping Human Antibodies for Therapy" (Nature 322:323–327), have described factors to be considered in choosing heavy- and light-chain polypeptides which may receive substituted CDRs in order to create another antibody with the same desired function as the antibody produced by the antibody-forming cell. Moreover, as described by Winter and colleagues (see E. S. Ward et al., Nature 341:544 1989; see also R. Orlandi et al., Proc, Natl. Acad. Sci. U.S.A. 86:3833 1989), in some cases significant capacity to bind antigen may reside in the CDRs of the heavy chain alone and dimers of heavy chains may bind usefully to antigens.

The amino acid sequence of the CDR may be determined by three general methods: (1) directly from amino acid sequence of the antibody produced by the antibody-forming cell; (2) from the RNA of the antibody-forming cell; or (3) from the DNA of the antibody-forming cell.

A. DETERMINATION OF THE VARIABLE REGION OR PORTION THEREOF FROM THE PARTIAL AMINO ACID SEQUENCE OF THE ANTIBODY PRODUCED BY THE ANTIBODY-FORMING CELL

The amino acid sequence of the variable region or a portion thereof which confers the desired function may be determined directly by at least two different methods. First, the antibody-forming cell may be grown to a sufficient density such that sequenceable quantities of antibodies are produced. In brief, cells are incubated for 3 days in nutrient medium such as Iscoves Modified Dulbecco's medium containing bovine serum albumin. Supernatants are collected and the bulk of the bovine serum albumin is removed using bovine serum albumin-specific antibodies coupled to a solid matrix. The supernatant is then subjected to SDS-PAGE under reducing conditions. Proteins are transferred by electroblotting to a membrane such as Sequelon (Milligen/Biosearch, Boston, Mass.), and bands corresponding to the position of heavy- and light-immunoglobulin chains are sequenced, as described by Aebersold et al. ("Covalent Immobilization of Proteins for High-Sensitivity Sequence Analysis: Electroblotting Onto Chemically Activated Glass From Sodium Dodecyl Sulfate-Polyacrylamide Gels," *Biochem.* 27:6860, 1988). Alternatively, if the antibody-forming cell grows slowly or produces only small amounts of antibody, the cell may be immortalized with any of the techniques well known in the art, such as the EB virus, electrofusion, fusion with a myeloma, in addition to stimulation with factors such as IL-1, IL-2, IL-4, IL-5, and IL-6. Furthermore, in contrast to techniques relying on the production of stable antibody producing cells- e.g., the hybridoma technology or EBV-transformation technology for producing monoclonal antibodies, the present invention does not require stability beyond the period necessary to generate sufficient antibody for sequencing.

B. DETERMINATION OF THE VARIABLE REGION OR PORTION THEREOF FROM THE RNA ENCODING PRODUCED BY THE ANTIBODY-FORMING CELL

Once an antibody-forming cell of a desired function has been identified, RNA is recovered from the cell by established methods, such as the method of Rappolee et al. (*J. Cell Biochem.* 39:1–11, 1989), or a scaled-down version of the method of Gonda et al. (*J. Virol.* 61.:2754–2763, 1987). The amino acid sequence may then be determined from the RNA which is produced by the antibody-forming cell by at least two different methods.

Within the first method, once RNA has been recovered, cDNA is constructed. Many methods for constructing cDNA from RNA are well known in the art, such as those described by Sambrook et al. (Sambrook, Fritsch and Maniatis, *Molecular Cloning—A Laboratory Manual*, Cold Spring Harbor Laboratory Press, 1989).

Preferably, the cDNA is then amplified using techniques well known in the art, such as Polymerase Chain Reaction (PCR). See Mullis, U.S. Pat. No. 4,683,195; Mullis et al., U.S. Pat. No. 4,683,195; and Mullis et al,. U.S. Pat. No. 4,800,159. See also H. A. Erlich (ed.), *PCR Technology*, Stockton Press, New York, N.Y., 1989; M. A. Innis et al. (eds.), *PCR Protocols: A Guide to Methods and Applications*, Academic Press, San Diego, Calif., 1989; H. A. Erlich (ed.), *Polymerase Chain Reaction: Current Communication in Molecular Biology*, Cold Springs Harbor Press, Cold Spring Harbor, N.Y., 1989. Briefly, cDNA segments encoding the portion of the antibody that confers the desired function are exponentially amplified by performing sequential reactions with a DNA polymerase. The reaction is primed by a 5' and a 3' DNA primer, the 3' antisense primer corresponding to a DNA sequence in the constant (or joining) region of the immunoglobulin chain and the 5' primer (or panel of related primers) corresponding to a DNA sequence in the variable region of the immunoglobulin chain. This combination of oligonucleotide primers has been used in the PCR amplification of murine immunoglobulin cDNAs of unknown sequence (see Sastry et at., Proc Natl. Acad. Sci. 86:5728–5732, 1989; and Orlandi et al., *Proc. Natl. Acad. Sci.* 86:3833–3837, 1989). When immunoglobulin cDNAs are amplified from species in which it is difficult to design adequate 5' primers, ie., where few immunoglobulin variable region sequences are known, an "anchored polymerase chain reaction" may be performed (see Loh et al., *Science* 243:217–220, 1989). In this procedure, the first strand cDNA is primed with a 3' DNA primer as above, and a poly(dG tail) is then added to the 3' end of the strand with terminal deoxynucleotidyl transferase. The product is then amplified by PCR using the specific 3' DNA primer and another oligonucleotide consisting of a poly(dC) tail attached to a sequence with convenient restriction sites.

The amino acid sequence encoding the portion of the antibody that confers the desired function may also be determined by a second method. The recovered RNA is first amplified with T7 or Q-fi replicase (see Lizardi et al., *Bio/Technology* 6:1197–1202, 1988). Briefly, a primer bearing a T7 promoter sequence, the left half of the MDV-1 sequence (the naturally occurring template for Q-β replicase) and a homologous sequence of the specific RNA being amplified is used to produce a cDNA copy of the specific RNA using an appropriate DNA polymerase. This extended first DNA is hybridized to a second DNA containing the right half of the MDV-1 sequence and a sequence homologous to the extended sequence of the first DNA. The second sequence is extended with a DNA polymerase. Incubation of these DNA complexes with T7 RNA polymerase results in synthesis of recombinant RNAs that can amplify exponentially by incubation with Q-β replicase. Once the amplified RNA has been recovered, cDNA may be constructed using the above-described methods.

Once the cDNA has been obtained using either of the above two methods, the nucleotide sequence may then be determined by established conventional methods. The amino acid sequence of the CDRs will then be evident from translation of the nucleotide sequence.

C. DETERMINATION OF THE VARIABLE REGION OR A PORTION THEREOF FROM THE DNA ENCODING THE ANTIBODY PRODUCED BY THE ANTIBODY-FORMING CELL

The amino acid sequence encoding the portion of the antibody that confers the desired function may also be determined from the DNA of the antibody-forming cell. Briefly, DNA is recovered from the cell using standard procedures. Clonal expansion with growth factors or fusion or immortalization of the cell as discussed above will enhance the yield of DNA. The specific DNA sequences encoding the rearranged V-regions including the CDRs are amplified by PCR and resulting DNA sequenced by standard procedures. The amino acid sequence of the variable region or portion thereof may be determined by translation of the nucleotide sequence of the DNA. Because this strategy may occasionally amplify a nonproductively rearranged V-region, it may be necessary to test the expression combination of the different variable heavy and light chains in a suitable cell and test for the production of the desired antibody in the indicator system.

Once the amino acid sequence of the variable region or portion thereof has been identified, the predicted DNA sequence corresponding to that of the amino acid sequence may be incorporated into a vector capable of directing the expression and secretion of the protein with a desired function.

The procedure described by Reichman et al. in "Reshaping Human Antibodies for Therapy," *Nature* 322:323–327, may be followed to substitute the portion of the antibody that confers the desired function for those of selected heavy- and light-immunoglobulin chain genes. Briefly, large mutagenic oligonucleotides corresponding to the complementarity determining regions of the heavy and light chains of the antibody in question are transferred to plasmids that contain genomic clones corresponding to a rearranged heavy-chain gene or rearranged light-chain gene, respectively.

The resultant heavy- and light-chain genes, now bearing the complementarity determining regions, may be expressed by the vectors in host cells by methods well known to those skilled in the art. Many suitable host cells may be utilized, including among others, bacterial, fungal, mammalian, and insect cells. The cell type (such as COS cells or CHO cells) may be selected according to the nature of the expression vector employed such that expression of the immunoglobulin is optimized. The cells are then transfected using standard methods which are well known to one of ordinary skill in the art. These methods include electroporation or transfection using calcium phosphate, DEAE dextran, or protoplast fusion methodologies (see Sambrook et al. supra.) Subsequently, proteins which are expressed by the host cell may be readily purified utilizing methods well known in the art (see generally, Sambrook et al. supra).

Alternatively, as discussed above, once the amino acid sequence of the portion of the antibody that confers the desired function has been determined, a protein may be synthesized directly, such that the synthetically constructed protein contains the amino acid sequence of the conferring the desired function. Methodologies for the efficient chemical synthesis of large proteins have been optimized by Clark-Lewis et al. (see Clark-Lewis et al., *Science* 231:134–139, 1986). A particularly preferred method is to synthesize and refold separately the variable regions of the heavy and light chains using the methods outlined by Clark-Lewis and colleagues (see Clark-Lewis, supra). Subsequently, the proteins are allowed to associate to form heavy chain- light chain dimers under conditions as described by E. A. Kabat in *Structural concepts in Immunology and Immunochemistry*, Holt, Rinehart & Winston, Inc., New York, N.Y., 1968, pp. 157–81.

Within one embodiment of the invention, the amino acid sequence may be optimized to enhance the desired function of the protein. Reichman et al. ("Reshaping Human Antibodies for Therapy," *Nature* 322:323–327) have outlined some of the factors to be considered in altering the amino acid sequence of the variable region. Additionally, the indicator systems described herein are powerful tools for screening proteins with variations in their amino acid sequence to identify variants with enhanced functional activities. For example, cells transfected with vectors with mutations that lead to changes in the amino acid sequence of the CDRs or other parts of the V-region and thus secreting proteins with potentially enhanced functional activity may produce larger plaques in the appropriate indicator system.

The desired function of the antibody produced by the antibody-forming cell may also be transferred into proteins other than complete immunoglobulin molecules. These proteins include active fragments of immunoglobulin molecules and analogs of immunoglobulins which are also able to provide a functional framework for the CDRs. These proteins may be expressed either in mammalian cells (see L. Reichman and *J. Foote, J. Molec. Biol.* 203:825–828, 1988) or in bacteria (see A. A. Sperra and A. Pluckthin, *Science* 240:1038–1041, 1988). Single chain molecules comprising the variable regions of heavy and light chains bridged by a polypeptide and produced as a single polypeptide (see J. S. Huston et al., *Proc. Natl. Acad. Sci. USA* 85:5879–5883, 1988) are another type of protein into which desired binding characteristics can be introduced by the present invention. Likewise, the desired binding characteristics can be transferred by this invention to fusion proteins in which the V-regions of heavy and light chains are fused to one another and to other functional domains or proteins such as toxins (see Vijay K. Chaudhary et al., *Nature* 339:394, 1989).

Vectors may also be produced which direct the expression of a protein with a desired function within a host cell, but in which the nucleotides encoding the signal sequences that direct secretion of the translated protein have been deleted. Such a vector will only direct expression of the protein within the cytoplasm of the host cell, and not secretion of the protein (see S. Biocca et al., *EMBO J.* 9(1):101–108, 1990). Suitable vectors directing the production of intracellular antibodies or antibody derived proteins into which the binding or other functional characteristics of an antibody have been introduced are useful, for example, in inhibiting the action of a particular protein in a cell and its progeny. Proteins that may be targeted include viral proteins essential for infection by the virus, so that by this means cells of animal or plant origin can be made resistant to infection by a virus, for example, HIV-1. Uses include the introduction of such vectors into the germline to produce disease-resistant transgenic animals or plants or into hemopoietic stem cells to produce an immune system in which T lymphocytes and other cells of hemopoietic origin are resistant to infection with a virus such as HIV.

Within a second methodology, as described in more detail below in the Examples, the variable region or a portion thereof (for example, the heavy-and light-chain variable regions) are subcloned into expression vectors designed to restore an appropriate leader sequence and an immunoglobulin-constant region of the chosen light- or heavy-chain class. Alternatively, the amplified cDNA corresponding to complete heavy and light chains is cloned and subcloned into an expression vector restoring a leader sequence. Such an expression vector would be based on an established vector into which a functional leader sequence had been introduced. Ligation of the light or heavy chains, their variable regions or portions thereof into this expression vector would reconstitute a functional signal peptide.

The following examples are offered by way of illustration, and not by way of limitation.

EXAMPLES

Example 1

Development of an Indicator System to Detect an Antibody-Forming Cell which Neutralizes Human IL-2

To identify an antibody that is able to neutralize the growth factor human interleukin-2, a cell-line such as CTLL-2 (ATCC No. TIB 214) that requires human IL-2 to live in culture systems, is washed three times and incubated for 4 hours at 37° C. in medium, washed again and suspended at $10^8$ per ml in warm (37° C.) medium containing RPMI-1640, 10% fetal bovine serum to which has been added a 1/10 volume of a sterile warm (40° C.) solution of 3% agar (DIFCO Laboratories, Mich.) in water, together with about 0.5 unit of human 1L-2 (Amgen, Sevenoaks, Calif.). This medium promotes 50% of maximal proliferation of this concentration of indicator cells and maintains completely their survival for 24 hours. A source of factors that can enhance the in vitro survival of antibody forming cells can be included; one such useful preparation for mouse antibody-forming cells is 10% by volume of a tenfold concentrate of medium conditioned by the murine cell-line 3T3 (ATCC No. CCL 92). Other useful additives are IL-1, IL-2GM-CSF, IL-4, IL-5, IL-6 and interferon-γ, usually of the species from which the antibody-secreting cells were derived. Antibody-forming cells are prepared from the spleen of a mouse immunized intraperitoneally three times at monthly intervals with human interleukin-2, 100 μg in 0.1 μl of Freund's incomplete adjuvant (Difco Laboratories, Mich.), and on the first occasion, in (0–1 ml of Freund's complete adjuvant (Difco Laboratories, Mich.). The presence of anti-IL-2 antibodies in the serum is confirmed by testing serum from the mouse for the capacity to inhibit IL-2 dependent proliferation of an IL-2 dependent such as CTLL-2, and to bind IL-2 in an ELISA assay. A mouse with the highest titres of IL-2 neutralizing activity is selected and is injected intravenously with 10 μg of interleukin-2. Four to seven days later, the spleen is removed and gently dissociated into a cell-suspension. Erythrocytes are lysed by brief exposure to 0.75% hypotonic ammonium chloride in 0.017 M Tris buffer (pH 7.2), leaving only nucleated spleen cells ("Selected Methods in Cellular Immunology," B. Mishell and S. Shiigi (eds.), W. H. Freeman and Co., San Francisco, 1980.

The nucleated spleen cells are added to the indicator system at final concentrations ranging from $10^4$/ml to $10^5$/ml. One ml of the mixture is applied to a warm (37° C.) glass slide or petri dish and after briefly storing at room temperature or in a cold room at 4° C. to allow the agar to set, the slide is incubated overnight at 37° C. in a humidified $CO_2$ incubator. The preparation is examined for the presence of plaques of dead cells, using an inverted microscope and phase contrast optics. Antibody-forming cells that have secreted a neutralizing antibody into their immediate environment are identified as central viable cells in plaques of dead cells.

Example 2

Development of an Indicator System to Detect Cells which Mimic Interleukin-2

To detect cells producing antibodies that mimic IL-2, cells that require IL-2 to survive such CTLL-2's, are incubated at a density of $2 \times 10^6$ cells per square centimeter, together with a source of nucleated spleen cells taken from an animal, e.g., a rat, immunized against the receptor for IL-2. This can be accomplished by immunization by standard techniques with CTLL-2, or a purified preparation of the receptor. The indicator system mixture is prepared with 0.3% agar and CTLL-2 indicator cells and a source of antibody-secreting cells as described above, except that no viability-sustaining factor such as IL-2 is included, and is layered on a transparent surface and incubated as described above. Cells producing antibodies that mimic IL-2 and produce the desired effect, in this instance of maintaining viability of the indicator cells, may be identified within plaques of surviving cells.

Example 3

Production of an Anti-Erythrocyte Antibody

A Balb/C mouse is immunized by intraperitoneal injection of $10^9$ sheep erythrocytes suspended in 0.2 ml of normal saline. Five days later, the mouse is sacrificed and the spleen removed. A single-cell suspension is prepared by gently mincing the spleen with scissors and pressing it through a wire sieve. The spleen cells are washed once with tissue-culture medium (RPMI-1640 with 10% fetal calf serum and 20 mM HEPES) and resuspended in 40 ml of this medium.

A mixture is prepared, consisting of spleen cells at $10^5$–$10^6$ per ml, a source of complement such as 15% (v/v) guinea pig serum preabsorbed twice with an equal volume of sheep erythrocytes, sheep erythrocytes at $5 \times 10^8$/ml, and an enhancing serum, e.g., 0.5% sheep anti-mouse immunoglobulin) in nutrient medium buffered with 20 mM HEPES. One to ten microliter aliquots of this mixture are introduced under a thin layer of paraffin oil (warmed to 37° C.) on a warm (37° C.) glass microscope slide which was incubated in a humidified incubator at 37° C. in 10% $CO^2$ and air for 30 minutes.

The slide is then placed on the stage of an inverted microscope. Areas where the sheep erythrocytes have been lysed by the action of antibody and complement ("plaques") are located under phase-contrast illumination. Plaques which the antibody-forming cell has formed can then be confidently identified through the following characteristics:

(a) Evidence of lysis rather than artifactual clearing of the erythrocytes in the form of lysed erythrocyte "ghosts."

(b) The presence in the plaque of a single, centrally located viable cell.

The ability of the identified cell to produce the desired antibody is confirmed by transferring it (using a fine glass pipette manipulated by a micromanipulator and connected to a syringe controlled by a micrometer) first into a droplet of medium on the slide to dilute out any carried-over antibody and a second time into a droplet containing sheep erythrocytes, guinea pig serum, and medium with enhancing serum as before (but no other cells) to confirm that this cell formed another plaque after incubation for 15 minutes.

This cell is then transferred (in a volume no greater than 20 µl of culture medium) to an eppendorf tube. To this tube is added 20 µl of Proteinase K (BDH Biochemicals) at 10 mg/ml and 100 ml of lysis buffer (10 mM Tris HCl pH 7.4, 100 mM NaCl 1 mM EDTA, 0.5% SDS). The solution is immediately vortexed vigorously then incubated at 37° C. for 60 minutes.

After this incubation a further 20 µl of 2.5M NaCl is added together with 50 µg of oligo-dT cellulose, and the mixture incubated overnight on a rotating wheel. The oligo-dT cellulose (and the bound polyadenylated RNA) is then pelleted by centrifugation, washed once with a wash buffer (10 mM Tris HCl pH 7.4, 500 mM NaCl 1 mM EDTA, 0.5% SDS), the supernatant discarded then the pellet washed again with a buffer comprising 100 mM NaCl and 10 mM Tris HCl (pH 7.4).

The polyadenylated RNA is then eluted from the oligo-dT cellulose by resuspension of the pellet in 15 µl of 10 mM Tris HCl (pH7.4). The oligo-dT cellulose is separated by centrifugation and the supernatant retained.

The eluted RNA is reverse-transcribed in a buffer consisting of 50 mM Tris HCl pH8.3, 75 mM KCl, 10 mM DTT, 3 mM MgCl$_2$, 0.5 mM each of dGTP dATP dTTP and dCTP, 200 u M-MLV reverse transcriptase and 1 mM of each specific antisense oligonucleotide primer. This reaction is performed in a total volume of 25 µl at 37° C. for 60 minutes.

The antisense (and sense) primers are designed to amplify the variable and constant regions of the immunoglobin heavy chains of classes mu and gamma, and the variable and constant regions of the immunoglobulin light chains of class kappa. The antisense primers used correspond to the 3' ends of the coding regions of the heavy and light chain mRNAs. A HindIII site is introduced after the stop codon to facilitate cloning of the PCR fragment into a pUC 12 vector.

These antisense oligonucleotide primers would be:
1. A primer for a Kappa light-chain constant region:
G AAG CTT CTA ACA CTC ATT CCT GTT GAA GCT CTT GAC
2. A primer recognizing all four c-terminal Gamma constant regions:
GAA CGT TCA TTT ACC (AC)GG AGA GCG GGA GAG GCT CTT [Interchangeable nucleotides are indicated in parentheses]
3. A primer recognizing the c-terminal Mu constant region:
GAA GCT TCA ATA GCA GGT GCC CCG TGT GTC AGA CAT The entire 25 µl from the reverse priming reaction is then transferred to a tube containing 25 mM TAPS pH 9.3, 2 mM MgCl$_2$, 50 mM KCl, 1 mM dithiothreitol, 2.5 u Taq DNA polymerase, 0.2 mM of each dATP, dCTP, dGTP and dTTP, and 1 mM of each specific sense oligonucleotide primer. The total volume for this reaction is 100 µl.

The sense oligonucleotide primers recognize regions of the variable region DNAs encoding the N terminal residues of the mature light and heavy chains. A HindHi site is introduced at the 5' end of each oligonucleotide primer to facilitate cloning of the PCR fragment into a pUC 12 vector.

These oligonucleotide primers would be:
1. A primer recognizing all Kappa variable regions:
CAA GCT TCC AGA (TG)GT GAC AT(CT) (AT)(AT)G ATG ACC GAG TCT CCA [Interchangeable nucleotides are indicated in parentheses]
2. A series of primers together able to recognize all heavy chain variable regions:

CAA GCT TCC GAG GTC CAG CTG GTG GAG TCT GG
CAA GCT TCC GAG GTC CAG CTG GTG GAG TCA GG
CAA GCT TCC GAG GTC CAG CTT GTG GAG TCT GG
CAA GCT TCC GAG GTC CAG CTT GTG GAG TCA GG
CAA GCT TCC GAG GTC CAA CTG GTG GAG TCT GG
CAA GCT TCC GAG GTC CAA CTG GTG GAG TCT GG
CAA GCT TCC GAG GTC CAA CTT GTG GAG TCT GG
CAA GCT TCC GAG GTC CAA CTT GTG GAG TCA GG

The tube is then placed in an automated thermal cycler, such as the Perkin-Elmer Cetus DNA Thermal Cycler (Norwalk Conn. Part No. N801-0055) and cycled for 60 cycles with a standard profile using an annealing temperature of 50° C. The reaction mix is then ethanol precipitated in the presence of 5 µg tRNA, resuspended in a total volume of 100 µl and digested to completion with HindIII. The digested DNAs are then separated by 1% agarose gel electrophoresis and the amplified light- and heavy-chain DNAs isolated from the gel. The light-chain DNA would be expected to be in the order of 600–700 bp and the heavy-chain DNA in the order of 1.3–1.7 kb.

Each of the light and heavy chains is cloned into the HindIII site of pUC12 by standard methods. (See Sambrook et al., *Molecular Cloning: A Laboratory Manual*, Cold Spring Harbor Laboratory Press, 1989). Each end of both chains is sequenced by double stranded sequencing using the standard dideoxy chain termination method. The sequencing has four purposes: first, to confirm that the bands are indeed immunoglobulin heavy and light chains; second, that the 5' primer has introduced the HindIII in the required frame (see below); third, that the 3' primer has introduced an in-frame stop codon; fourth, to locate convenient restriction sites with which to determine orientation of the insert when subcloned into the expression vector.

The light- and heavy-chain DNA sequences are then transferred from the pUC12 vector to the HindIII site of the expression vector p587L (see Gunning et al., *Proc. Natl. Acad. Sci.* 84:4831–4835, 1987) using standard methods. This vector is based on the p587 expression vector in which the leader sequence of the murine IL-3 gene has been inserted. Ligation of the light or heavy chain into this p587L vector, in the correct orientation, will reconstitute a functional signal peptide. Orientation is determined by digestion with the restriction endonuclease found to be convenient on DNA sequencing, followed by separation of the digested fragments by agarose gel electrophoresis.

The separate light- and heavy-chain expression constructs are expanded in *E. coli* and purified by standard methods. These two expression constructs are then mixed in equimolar amounts and transfected into COS-7 cells for expression. This transfection is performed by a standard calcium phosphate precipitation method. Twelve hours after transfection, the culture medium is changed and the cells cultured for a period of 3 days.

Conditioned medium from these cultures is collected and the protein is purified using an immuno-affinity column coupled with antibodies specific for the protein. Such antibodies could include antibodies specific for the variable region, framework region, or part of the constant region of immunoglobulin derived from the same species as the DNA sequences in the vector into which oligonucleotides corresponding to the CDRs of the prototypic had been inserted. Affinity chromatography using a column coupled with the substance to which the antibody binds may also be utilized to purify the antibody.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for producing an antibody, antibody variable region, or a portion thereof which has an antibody binding region with a desired function, comprising:

(a) obtaining from a warm-blooded animal a population of antibody-forming B cells or antibody-forming progeny thereof wherein the B cells or progency thereof are non-hybridoma or non-Epstein Barr virus (EBV) transformed, and wherein the B cells or progency thereof contain at least one cell that produces an antibody exhibiting a desired function, followed by;

(b) suspending the population of antibody-forming B cells or progency thereof in a medium, the medium having an indicator system incorporated therein which indicates the presence and location of a cell which forms antibodies exhibiting the desired function;

(c) identifying a cell forming an antibody exhibiting the desired function;

(d) isolating the identified antibody-forming cell from the medium;

(e) determining the amino acid sequence of the variable region or a portion thereof which exhibits the desired function of the antibody produced by the isolated antibody-forming cell; and (f) synthesizing an antibody, antibody variable region, or a portion thereof which has the amino acid sequence of the variable region or portion thereof which exhibits the desired function.

2. A method for producing an antibody, antibody variable region, or a portion thereof which has an antibody binding region with a desired function, comprising:

(a) obtaining from a warm-blooded animal a population of antibody-forming B cells or antibody-forming progeny thereof, wherein the B cells or progeny thereof are non-hybridoma or non-EBV transformed, and wherein the B cells or progeny thereof contain at least one cell that produces an antibody exhibiting a desired function, followed by;

(b) suspending the population of antibody-forming B cells or progeny thereof in a medium, the medium having all indicator system incorporated therein which indicates, the presence and location of a cell which forms antibodies exhibiting the desired function;

(c) identifying a cell forming an antibody exhibiting the desired function;

(d) isolating the identified antibody-forming cell from the medium;

(e) determining the amino acid sequence of the variable region or a portion thereof which exhibits the desired function of the antibody produced by the isolated antibody-forming cell;

(f) incorporating the DNA sequence corresponding to the amino acid sequence of said variable region or portion thereof conferring the desired function into a vector which directs the expression and secretion of said antibody, antibody variable region, or a portion thereof which has an antibody binding region with a desired function;

(g) transletting said vector into a host cell;

(h) growing said host cells in an appropriate medium; and (i) isolating the antibody, antibody variable region, or a portion thereof which has an antibody binding region with the desired function.

3. The method of claims 1 or 2 including, subsequent to the step of isolating the antibody-forming cell:

(a) recovering RNA from said isolated antibody-forming cell;

(b) generating cDNA from said RNA; and (c) amplifying the cDNA of the variable region or a portion thereof which confers the desired function of the antibody produced by the isolated antibody-forming cell.

4. The method of claims 1 or 2 including, subsequent to the step of isolating the antibody-forming cell:

(a) recovering RNA from said isolated antibody-forming cell;

(b) amplifying the RNA of the variable region or a portion thereof which confers the desired function of the antibody produced by the isolated antibody-forming cell; and (c) generating cDNA from said RNA.

5. The method of claims 1 or 2 including, subsequent to the step of isolating the antibody-forming cell:

(a) recovering DNA from said isolated antibody-forming cell; and (b) amplifying the DNA of the variable region or a portion thereof which confers the desired function of the antibody produced by the isolated antibody-forming cell.

6. A method for producing an antibody, antibody variable region, or a portion thereof which has an antibody binding region with a desired function, comprising:

(a) obtaining from a warm-blooded animal a population of antibody-forming B cells or antibody-forming progeny thereof, wherein the B cells or progeny thereof are non-hybridoma or non-EBV transformed, and wherein the B cells or progeny thereof contain at least one cell that produces an antibody exhibiting a desired function; followed by (b) suspending the population of antibody-forming B cells or progeny thereof in a medium, the medium having an indicator system incorporated therein which indicates the presence and location of a cell which forms antibodies exhibiting the desired function;

(c) identifying a cell forming an antibody exhibiting the desired function;

(d) isolating the identified antibody-forming cell from the medium;

(e) recovering RNA from said isolated antibody-forming cell;

(f) generating cDNA from said RNA;

(g) amplifying the cDNA of the variable region or a portion thereof which confers the desired function of the antibody produced by the isolated antibody-forming cell;

(h) incorporating the amplified cDNA into a vector capable of directing the expression and secretion of an antibody, antibody variable region, or a portion thereof which has an antibody binding region with the desired function;

(i) transfecting said vector into a host cell;

(j) growing said host cells in an appropriate medium; and (k) isolating the antibody, antibody variable region, or a portion thereof which has an antibody binding region with the desired function from said host cell.

7. A method for producing an antibody, antibody variable region, or a portion thereof which has an antibody binding region with a desired function, comprising:

(a) obtaining from a warm-blooded animal a population of antibody-forming B cells or anti-forming progeny thereof, wherein the B cells or progeny thereof are non-hybridoma or non-EBV transformed, and wherein the B cells or progeny thereof contain at least one cell that produces an antibody exhibiting a desired function, followed by;

(b) suspending the population of antibody-forming B cells or progeny thereof in a medium, the medium having an indicator system incorporated therein which indicates the presence and location of a cell which forms antibodies exhibiting the desired function;

(c) identifying a cell forming an antibody exhibiting the desired function;

(d) isolating the identified antibody-forming cell from the medium;

(e) recovering RNA from said isolated antibody-forming cell;

(f) amplifying the RNA of the variable region or a portion thereof which confers the desired function of the antibody produced by the isolated antibody-forming cell;

(g) generating cDNA from said RNA;

(h) incorporating the cDNA into a vector capable of directing the expression and secretion of an antibody, antibody variable region, or a portion thereof which has an antibody binding region with the desired function;

(i) transfecting said vector into a host cell;

(j) growing said host cells in an appropriate medium; and (k) isolating the antibody, antibody variable region, or a portion thereof which has an antibody binding region with the desired function from said host cell.

8. The method of claims 1, 2, 6, or 7 wherein said medium is selected from the group consisting of a layer of gelified media and a layer of liquid media.

9. The method of claim 8 wherein the medium is a nutrient medium.

10. The method of claim 8 wherein the gelified media comprises about 0.3% to 0.6% agar or about 1.0% methyl cellulose.

11. The method of claims 1, 2, 6, or 7 wherein the antibody-forming B cells or progeny thereof are obtained from an animal which has been immunized with a selected antigen.

12. The method of claim 11 wherein the antigen is selected from the group consisting of erythropoietin, erythropoietin receptors, colony-stimulating factors, and viral antigens.

13. The method of claims 1, 2, 6, or 7 wherein the antibody-forming B cells or progeny thereof are obtained from an animal which generated said cells during the course of a selected disease.

14. The method of claims 1, 2, 6, or 7 wherein said animal is a warm-blooded animal selected from the group consisting of rabbits, humans, mice, rats, sheep, cows, and pigs.

15. The method of claims 1, 2, 6, or 7, including, subsequent to the step of isolating an identified antibody-forming cell, enriching the population of antibody-forming cells by exposure to bovine serum albumin or Percoil gradient.

16. The method of claims 1, 2, 6, or 7 wherein the indicator system comprises a layer of cells whose growth, viability, or function is affected by antibodies exhibiting a desired function produced by the isolated antibody-forming cell.

17. The method of claims 1, 2, 6, or 7 wherein the antibody which exhibits a desired function exhibits biological activity analogous to a protein selected from the group consisting of IL-1α, IL-1β, IL-2, IL-3, IL-4, IL-5, IL-6, IL-7, IFN-α, IFNγ, G-CSF, M-CSF, GM-CSF, TNF-α, TGFβ, erythropoietin, EGF, PDGF, and the ligand of the kit protein.

18. The method of claims 1, 2, 6, or 7 wherein the indicator system comprises one or more pathogenic microorganisms, and a layer of cells susceptible to infection by said microorganisms, wherein said antibodies exhibiting a desired function are identified as those which effect the pathogenicity of the microorganism.

19. The method of claim 18 wherein the layer of cells is adhered to a glass slide or petri dish.

20. The method of claims 1, 2, 6, or 7 wherein the indicator system comprises a set of two cell types selected from the group consisting of cells of distinct HLA histocompatibility antigen types, blood group antigen types, and tumor cells and normal cells of the same lineage, wherein said antibodies exhibiting a desired function are identified as those which agglutinate or lyse one cell of the two cell types.

21. The method of claim 20 wherein one of said cell types is labeled.

22. The method of claims 1, 2, 6, or 7 wherein the indicator system comprises erythrocytes or other particles coated with antigen, and said antibody exhibiting a desired function is identified as that which binds to the antigen, thereby causing the particles to agglutinate.

23. The method of claims 1, 2, 6, or 7 wherein the indicator system comprises erythrocytes or other particles coated with antigen, and said antibody exhibiting a desired function is identified as that which binds to the antigen, lysing the cells or particles in the presence of complement.

24. The method of claim 23 wherein the erythrocytes or other particles are coated with antigen utilizing a biotin/avidin coupling system.

25. The method of claim 23 wherein the indicator system further comprises anti-immunoglobulin antibodies such that complement fixation is enhanced.

26. The method of claims 1, 2, 6, or 7 wherein the indicator system comprises a complexing factor, and said antibody-forming cell is identified as that which binds to the complexing factor, forming a rosette.

27. The method of claim 26 wherein the complexing factor is an erythrocyte coupled to an antigen.

28. The method of claim 26 wherein the complexing factor is a particle coupled to an antigen.

29. The method of claim 26 wherein the complexing factor is a microorganism.

30. The method of claims 1, 2, 6, or 7 wherein the indicator system comprises a substrate, and said antibody exhibiting a desired function is identified as that which modifies the substrate in a detectable manner.

31. The method of claim 30 wherein the substrate is a chromogenic substrate, and wherein said chromogenic substrate is modified to produce a detectable color change in the vicinity of the antibody-forming cell.

32. The method of claim 30 wherein the substrate is a fluorogenic substrate, wherein said fluorogenic substrate is modified to produce a detectable change in fluorescence in the vicinity of the antibody-forming cell.

33. The method of claim 30 wherein the substrate is a colored substrate, wherein said colored substrate is modified to produce a detectable loss of color in the vicinity of the antibody-forming cell.

34. The method of claim 30 wherein the substrate is a fluorescent substrate, and wherein said fluorescent substrate is modified to produce a detectable loss of fluorescence in the vicinity of the antibody-forming cell.

35. The method of claim 30 wherein the antibody exhibiting a desired function cleaves the substrate, the product of this reaction allowing the detection of said antibody upon the addition of a reagent selected from the group consisting of stains, and, labeled antibodies.

36. The method of claim 30 wherein the substrate is a precursor of the hemolytic toxin aerolysin and wherein said antibody exhibiting a desired function is identified as that which cleaves said precursor, thus activating the toxin.

37. The method of claims 1, 2, 6 or 7 wherein the indicator system is positioned contiguous to the medium.

38. The method according to any one of claims 1, 2, 6 or 7, further comprising, prior to the step of obtaining a population of non-hybridoma antibody forming cells, immunizing a warm-blooded animal with a selected antigen.

* * * * *

UNITED STATES PATENT AND TRADEMARK OFFICE
CERTIFICATE OF CORRECTION

PATENT NO.    : 5,627,052
DATED         : May 6, 1997
INVENTOR(S)   : John W. Schrader It is certified that error appears in the above identified patent and that said Letters Patent is hereby corrected as shown below:

In column 25, claim 2, line 52, after "having" delete "all" and substitute therefor -- an --.

In column 26, claim 2, line 5, after "(g)" delete "transletting" and substitute therefor -- transfecting --.

In column 27, claim 15, line 66, after "or" delete "Percoil" and substitute therefor -- Percoll --.

In column 29, claim 35, line 13, after "of" delete "stains, and," and substitute therefor -- stains and --.

Signed and Sealed this

Fourteenth Day of July, 1998

*Attest:*

BRUCE LEHMAN

*Attesting Officer*    *Commissioner of Patents and Trademarks*